US005705157A

United States Patent [19]

Greene

[11] Patent Number: 5,705,157

[45] Date of Patent: Jan. 6, 1998

[54] METHODS OF TREATING CANCEROUS CELLS WITH ANTI-RECEPTOR ANTIBODIES

[75] Inventor: Mark I. Greene, Penn Valley, Pa.

[73] Assignee: The Trustees of the University of Pennsylvania, Philadelphia, Pa.

[21] Appl. No.: 347,018

[22] Filed: Nov. 30, 1994

Related U.S. Application Data

[63] Continuation of Ser. No. 386,820, Jul. 27, 1989, abandoned.

[51] Int. Cl.[6] .................... A61K 39/395; C07K 16/28; C07K 16/30

[52] U.S. Cl. .................... 424/138.1; 424/143.1; 424/155.1; 530/387.7; 530/388.22; 530/388.8; 530/388.85

[58] Field of Search .................... 424/138.1, 143.1, 424/155.1; 530/387.7, 388.22, 388.8, 388.85; 435/240.27

[56] References Cited

U.S. PATENT DOCUMENTS 4,444,744 4/1984 Goldenberg .
5,171,665 12/1992 Hellstrom et al. .................... 435/7.23

OTHER PUBLICATIONS

Harris et al., Tibtech 11:42–44, 1993.
Seaver, Genetic Engineering News 14: pp. 10 & 21, 1994.
Wawrzynzak, et al. Clin Exp Immunol 82:189–93, 1990.
Osband et al. Immunol. Today 11:193–5, 1990.
Schlom in "Molecular Foundations of Oncology", Boder, Ed., Williams & Wilkins, 1991, pp.95–134.
Dillman, J. Clin Oncol. 12:1497–1515, 1994.
Bargmann et al., "The neu Oncogene Encodes an Epidermal Growth Factor Receptor-related Protein", Nature vol. 319, pp. 226–230 (1986).
Bargmann et al., "Increased Tyrosine Kinase Activity Associated with the Protein Encoded by the Activated neu Oncogene", Proc. Natl. Acad. Sci. USA, vol. 85, pp. 5394–5398 (1988).
Bookman et al., "Immunotoxins Directed Against c-erbB2: Limited Activity Due to Poor Internalization" Third International Symposium on Immunotoxins p. 15 (1992).
Ceriani et al., "An Experimental Model for the Immunological Treatment of Breast Cancer" Proc. International Workshop on Molecular Antibodies 248–268 (1984).
Dillman, "Monoclonal Antibodies for Treating Cancer" Annals of Internal Medicine 111: 592–603 (1989).
Drebin et al., "Down-Modulation of an Oncogene Protein Product and Reversion of the Transformed Phenotype by Monoclonal Antibodies" Cell 41: 695–706 (1985).
Drebin et al., "Inhibition of Tumor Growth by a Monoclonal Antibody Reactive with an Oncogene-Encoded Tumor Antigen" PNAS USA 83: 9129–9133 (1986).
Drebin et al., "Monoclonal Antibodies Identify a Cell-Surface Antigen Associated with an Activated Cellular Oncogene" Nature 312: 545–548 (1984).
Fendly et al., "Characterization of Murine Monoclonal Antibodies Reactive to Either the Human Epidermal Growth Factor Receptor or HER2/neu Gene Product" Cancer Res. 50: 1550–1557 (1990).
Gorman et al, J. Cell Biochem. Supplement 12A C 219.
Hird et al., pp. 183–189 in Carney et al. Eds., "Genes and Cancer" John Wiley & Sons, 1990.
Houghton et al., "Monoclonal Antibodies: Potential Applications to the Treatment of Cancer" Seminars in Oncology 13: 165–179 (1986).
Hudziak et al., "$p185^{HER2}$Monoclonal Antibody Has Antiproliferative Effects in Vitro and Sensitizes Human Breast Tumor Cells to Tumor Necrosis Factor" Molec. and Cell. Biol. 9: 1165–1172 (1989).
Hung et al., "Molecular Cloning of the Neu Gene: Absence of Gross Structural Alteration in Oncogenic Alleles" PNAS USA 83: 261–264 (1986).
Kokai et al., "Stage-and Tissue-specific Expression of the Neu Oncogene in Rat Development" Proc. Natl. Acad. Sci. USA 84: 8498–8501 (1987).
Richert et al., "Epidermal Growth Factor Receptor" J. of Biol. Chem. 258: 8902–8907 (1983).
Rodeck et al., "Tumor Growth Modulation by a Monoclonal Antibody to the Epidermal Growth Factor Receptor: Immunologically Mediated and Effector Cell-Independent Effects" Cancer Res. 47: 3692–3696 (1987).
Ullrich et al., "Human Epidermal Growth Factor Receptor cDNA Sequence and Aberrant Expression of the Amplified Gene in A431 Epidermoid Carcinoma Cells" Nature 309: 418–425 (1984).
Waldmann, "Monoclonal Antibodies in Diagnosis and Therapy" Science 252: 1657–1662 (1991).
Wright et al., "Expression of c-erbB-2 Oncoprotein: A Prognostic Indicator in Human Breast Cancer" Cancer Res. 49: 2087–2090 (1989).
Waldmann, "The Interleukin-2 Receptor: A Target for Immunotherapy of Leukemia/Lymphoma" J. Cell. Biochem. Supp 18D: #R008 p. 100 (1994).
Hynes et al., "Recombinant Single Chain Immunotoxins Specific for EGF & ERBB-2 Receptors Inhibit in Vivo and in Vitro Tumor Cell Growth" J. Cell. Biochem. Supp 18D: #Y208 p. 237 (1994).

(List continued on next page.)

*Primary Examiner*—Toni R. Scheiner
*Attorney, Agent, or Firm*—Woodcock Washburn Kurtz Mackiewicz & Norris LLP

[57] ABSTRACT

The present invention provides methods and therapeutic compositions for treatment of mammalian tumors wherein the cells of such tumor express both epidermal growth factor receptor and p185neu, p185c-neu or a homologue of p185neu or p185c-neu and the epidermal growth factor. At least one antibody specific for epidermal growth factor receptor, monoclonal antibody 425, and at least one antibody specific for p185neu, p185c-neu or a homologue of p185neu or p185c-neu, monoclonal antibody 7.16.4, are administered to the mammal in an amount effective to reduce tumor growth.

6 Claims, 1 Drawing Sheet

OTHER PUBLICATIONS

Dougall et al., "Modulation of p185$^{c-erb-2}$ Expression and Tumorigenic Growth by Anti-Receptor Monoclonal Antibodies" J. Cell. Biochem. Supp 18D: #Y507 p. 252 (1994).

Mattern et al., "Human Tumor Xenografts as Model for Drug Testing" Cancer and Metastasis Reviews 7: 263–284 (1988).

Kuroiwa, T. et al., Abstracts of the 4th International Symposium on Pediatric Neuro-Oncology pp. 108–109.

Kokai, Y. et al., "Synergistic Interaction of p185c-nsu and the EGF Receptor Leads to Transformation of Rodent Fibroblasts" Cell 58: 287-292 (1989).

Wada, T. et al., "Anti-Receptor Antibodies Reverse the Phenotype of Cells Transformed by Two Interacting Proto-Oncogene Encoded Receptor Proteins" Oncogene 5: 489–495 (1990).

Wada, T. et al., "Intermolecular Association of the p185$^{neu}$ Protein and EGF Receptor Modulates EGF Receptor Function" Cell 61: 1339–1347 (1990).

Qian et al., "p185$^{c-neu}$ and epidermal growth factor receptor associate into a structure composed of activated kinases" PNAS USA 89: 1330–1334 (1992).

Slamon, "Role of the HER-2/neu Gene in Human Breast and Ovarian Cancer" from a Meeting of the American Association of Clinical Research (1992).

Buhrow et al., "Affinity Labeling of the Protein Kinase Associated with the Epidermal Growth Factor Receptor in Membrane Vesicles from A431 Cells" J. of Biol. Chem. 257: 4019–4022 (1982).

Downward et al, "Close similarity of epidermal growth factor receptor and v-erb-B oncogene protein sequences" Nature 307: 521-527 (1984).

Shih et al., "Transforming Genes of Carcinomas and Neuroblastomas Introduced into Mouse Fibroblasts" Nature 290: 261–264 (1981).

Takebe et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat" Mol. and Cell. Biol. 8: 466–472 (1988).

Yamamoto et al., "High Incidence of Amplification of the Epidermal Growth Factor Receptor Gene in Human Squamous Carcinoma Cell Lines" Cancer Res. 46: 414–416 (1986).

METHODS OF TREATING CANCEROUS CELLS WITH ANTI-RECEPTOR ANTIBODIES

This is a continuation of application Ser. No. 07/386,820, filed Jul. 27, 1989, now abandoned.

FIELD OF THE INVENTION

The present invention is related to the field of treatments of mammalian tumors. More particularly this invention relates to methods for treating mammalian tumors employing antibodies and novel therapeutic compositions for such treatment.

REFERENCE TO RELATED APPLICATIONS

This application is related to co-pending U.S. application Ser. No. 126,572 filed Nov. 30, 1987 in the names of Mark I. Greene and Jeffrey A. Drebin.

BACKGROUND OF THE INVENTION

Current tumor treatments rely for the most part in the cytotoxic effects of drugs and radiological therapy. Although these treatments bring remission and cure to some patients, they unfortunately have serious side effects because they kill not only tumor cells but also normal non-tumorous cells. There exists a great need for mammalian tumor treatments which affect primarily the tumor cells, but that have minimal interference with normal cells and cellular functions.

Recent studies in the molecular genetics of cancer indicate that certain genes known as oncogenes may play a role in the transformation of some cells from their normal condition to a cancerous condition. Proto-oncogenes, genes closely related to these genes, are found in somatic cells of all eukaryotic species examined and have been highly conserved in evolution and it is thought that proto-oncogenes normally play critical roles in cellular growth and development. Oncogene amplification and chromosomal rearrangements involving oncogenes have been detected in a large number of tumors. Furthermore, some tumors have been shown to contain activated oncogenes which, in DNA transfection assays, are capable of conferring neoplastic properties upon non-neoplastic rodent fibroblast cell lines. Collectively these studies suggest that alterations in proto-oncogene structure and function play a critical role in the development of neoplasia.

Although most oncogene-encoded proteins reside in the nucleus or the cytoplasm, some oncogenes encode proteins that express antigenic sites on the cell surface. For example, the erbB, fms and ros oncogene products are transmembrane glycoproteins that possess extracellular domains. The sis oncogene product may also exist in a membrane associated form on the surface of transformed cells. Another oncogene which encodes a protein that exposes antigenic sites on the surface of transformed cells has been identified by transfection of DNA from ethyl nitrosourea-induced rat neuroblastomas into NIH3T3 cells. This oncogene has been termed neu. The neu gene has been found to be amplified in some human tumors, particularly those of the breast, suggesting that this gene may play a role in the etiology of human cancer.

Amplification of c-erB-2, the human homologue of the rat c-neu gene, occurs with high frequency in some human adenocarcinomas of the breast, pancreas and ovary. Increasing c-erbB-2 expression levels may correlate with the clinical progression of adenocarcinoma of the breast. The neu oncogene and p185 have also been found active in human adenocarcinomas including breast, lung, salivary gland and kidney adenocarcinomas, as well as prostate neuroblastoma. In human primary breast cancers, amplification of the neu oncogene was found in about 30% of all malignant tumors examined. Increased malignancy, characterized by large tumor size and increased number of positive lymph nodes as well as reduced survival time and decreased time to relapse, was directly correlated with an increased level of amplification of the neu gene. The neu proto-oncogene is expressed at low levels in normal human tissues.

The neu oncogene was originally isolated from rat neuroblastomas that developed in the offspring of rodents exposed to ethylnitrosourea at a discrete time period of gestation. The neu oncogene encodes an 185 Kd surface glycoprotein, termed p185neu, that possesses tyrosine kinase activity, and is structurally similar to the EGF receptor at the nucleotide and amino acid level. However, p185neu has been shown to be distinct from the EGF receptor by detailed molecular analysis and chromosomal localization studies. The rodent cellular neu cDNA has been compared to the oncogenic neu cDNA, and the normal cellular gene product, p185c-neu, has been found to differ from the oncogene product by a single amino acid substitution (valine to glutamic acid) in the transmembrane anchoring domain. p185neu becomes activated by this point mutation in its transmembrane region. p185c-neu has been found in variety of tissues derived from developing and adult animals in a developmental stage and tissue specific manner. Both p185neu and its normal, cellular homologue, termed p185c-neu, possess tyrosine kinase activity, although the oncogenic form has greater, kinase activity. The neu encoded tyrosine kinase domain identifies the neu gene as a member of a large tyrosine kinase gene family. p185c-neu is highly homologous to, yet distinct from the epidermal growth factor receptor (EGFR).

The epidermal growth factor receptor protein is a structure of 170 kd mass that has been identified on both normal glial and glioma cells. Analysis of the EGF receptor's (EGFR) deduced primary structure suggests that is a transmembrane glycoprotein receptor which contains a tyrosine kinase domain. The extracellular portion of 621 amino acids of this receptor, which spans the membrane only once, makes up the ligand binding domain. By analysis of shared sequences, it has been determined that the EGF receptor is the proto-oncogene product of the transforming v-erbB oncogene. The v-erbB oncogene was first characterized from the avian erythroblastosis virus. The EGF receptor encoding gene is often found in amplified forms in glioblastoma. The EGF receptor is structurally and antigenically related to the neu oncogene encoded receptor. Despite structural similarities, neu and erbB also differ and are separated in the genome. The erbB gene has been mapped to human chromosome 6, whereas the neu gene resides on chromosome 17.

In in vitro studies, c-erbB-2 transfection and subsequent overexpression of p185c-erbB-2 results in transformation of NIH3T3m cells. Similar studies with overexpressed EGFR reveal EGF-dependent cell transformation in vitro assays, but these same cells are not tumorigenic in nude mice. Unlike the NIH3T3 erbB-2 transfectants, NIH3T3 cell lines expressing high levels of p185c-neu are not transformed.

EGF, in an EGFR dependent manner, stimulates normal and transformed rodent and human cell lines resulting in increasing tyrosine phosphorylation of p185neu, p185c-neu, and p185c-erbB-2 with a concomitant increase in their respective tyrosine kinase activities.

SUMMARY OF THE INVENTION

The invention provides novel methods for treating mammalian tumors expressing both the epidermal growth factor receptor and p185 neu, p185c-neu, or a homologue of p185 neu or p185c-neu, such as erbB-2 on the surface of tumor cells. At least one antibody specific for epidermal growth factor receptor and at least one antibody specific for p185 neu, p185c-neu or a homologue of p185 neu or p185c-neu are administered to the mammal in an amount effective to suppress tumor growth. The antibodies work synergistically to suppress tumor growth; the administration of a combination of antibodies having a greater effect in reducing tumor growth than the administration of either type of antibody alone. The antibodies are preferably specific for an external domain of the epidermal growth factor receptor and p185 neu, p185c-neu, or homologue of p185 neu or p185c-neu.

The invention also provides novel therapeutic compositions for treating mammalian cancer tumors having cells which express both the epidermal growth factor and p185 neu, p185c-neu or homologue of p185 neu or p185c-neu. The compositions of the invention comprise at least one antibody specific for p185 neu, p185c-neu or homologue of p185 neu or p185c-neu, at least one antibody specific for epidermal growth factor receptor and a pharmaceutically acceptable carrier or diluent.

It has been found that two distinct overexpressed tyrosine kineses, p185c-neu and EGFR can act synergistically to transform NIH 3T3 cells, thus identifying a novel mechanism that can lead to transformation of cells. Overexpression of p185c-neu alone in rodent fibroblasts does not result in a transformed cellular phenotype; nor does overexpression of EGFR alone. However, overexpression of both EGFR and p185c-neu in the same cell does result in cellular transformation.

Applicant has also demonstrated that administration of a mixture of antibodies specific for extracellular domains of EGFR and p185neu surprisingly have a synergistic effect in reducing or abolishing cancer tumor growth in mice. Administration of a mixture of both types of antibodies slow tumor growth to a much greater degree than administration of antibodies to either EGFR or p185neu alone.

In general, the antibodies used for tumor immunotherapy by passive transfer of monoclonal antibodies are specific against random structures on the malignant cell surface, rather that cell surface molecules required for maintenance of the transformed phenotype. Antibodies specific for structures that themselves are necessary for neoplastic cell function, as are EGFR and p185c-neu, represent a more potent and efficient approach to cancer treatment.

The methods of the invention are useful in treating mammalian cancer tumors expressing both EGFR and p185neu, p185c-neu, or a homologue of p185c-neu or p185neu, such as erbB-2, the human homologue. Human tumors often have elevated levels of c-erbB-2 and/or EGFR.

DETAILED DESCRIPTION OF THE INVENTION

Figure 1:
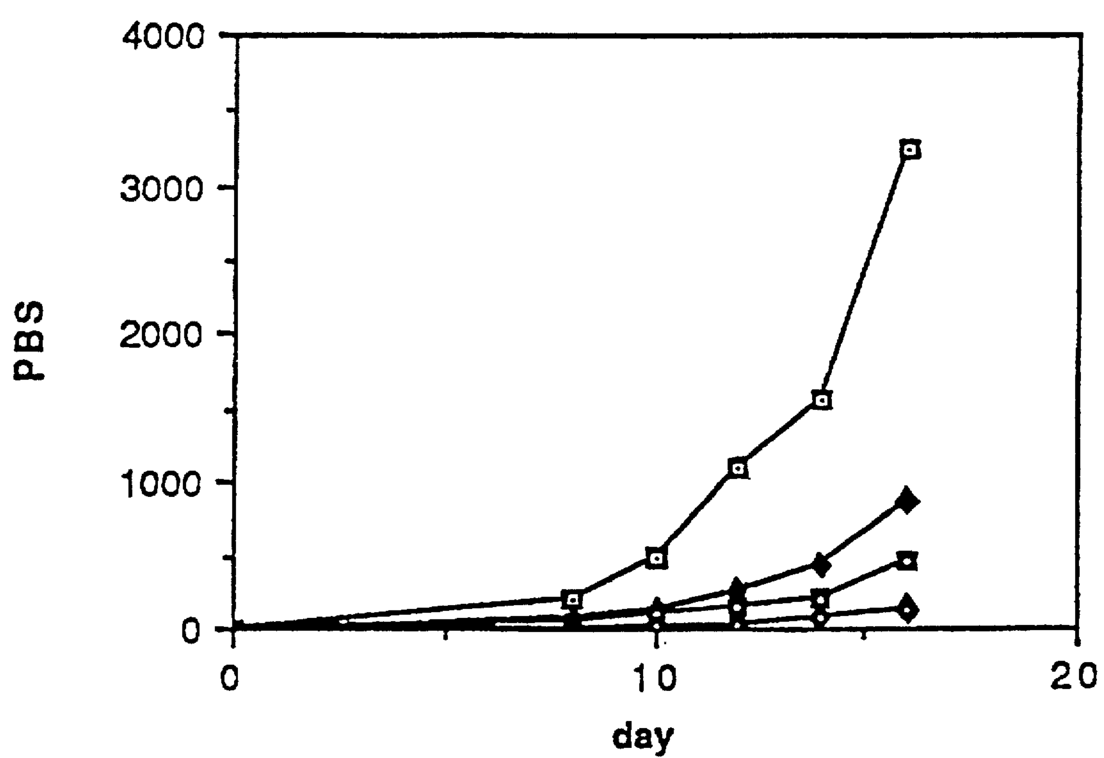
FIG. 1 shows a graph of the effects of monoclonal antibodies to EGFR and p185c-neu and a combination of these antibodies upon tumor growth.

In the methods of the invention antibodies, preferably monoclonal antibodies, are administered to mammals having a tumor expressing both epidermal growth factor receptors (EGFR) and p185 neu, p185c-neu or homologue of p185 neu or p185c-neu on the cell surfaces in amount effective to reduce tumor size.

Antibodies to EGFR and p185 neu, p185c-neu or homologue of p185 neu or p185c-neu are preferably administered to the mammal in combination with a pharmaceutically acceptable diluent or carrier, such as a buffer or saline solution. The antibodies may be administered to the mammal mixed together in the same diluent or carrier as a single dose, or they may be administered to the mammal in separate diluent or carrier solutions as separate doses, at substantially the same time or at different times. The antibodies are preferably administered to the mammal by injection into the tumor or tissue near the tumor. Other suitable methods of administration include oral, intraperitoneal, intramuscular and other conventional routes of pharmaceutical administration. The antibodies are administered to the mammal for a length of time effective to reduce tumor size and as needed to maintain regression of the tumor.

Antibodies useful in the methods of the invention may be made by conventional methods of producing monoclonal or polyclonal antibodies, such as the method in Harlow and Lane, eds., Antibodies: A Laboratory Manual, Cold Spring Harbor Laboratory, Cold Spring Harbor, N.Y., 1988. A general method for the production of monoclonal antibodies comprises the steps of immunizing an animal such as a mouse or rat with an antigen to which monoclonal antibodies are desired. After allowing time for the immune system to generate lymphocytes capable of producing antibodies to the antigen, the animal is sacrificed and a suspension of spleen cells is prepared. The spleen cells are then fused with myeloma cells by contacting them in the presence of a fusion promoter such as polyethylene glycol. A percentage of the cells fuse to produce hybridomas. The earlier immunization of the animal from which the spleen cells were removed results in a number of lymphocytes which secrete antibody to the antigen of interest, a characteristic that is transferred genetically to the hybridoma during fusion of the spleen and myeloma cells. Hybridomas secreting monoclonal antibody having the desired specificity are then isolated using routine screening techniques.

Antibodies suitable for use in the methods of the invention are preferably specific for extracellular domains of the receptor i.e., these portions of the molecule which extend beyond the transmembrane region into the extracellular region. The extracellular domains of the EGFR are amino acids 1 through 621, Ullrich et al. Nature 309: 418–425. The extracellular domains of p185c-neu are amino acids 1–657, Bargmann et al. (1986) Nature 319: 226–230. Antibodies to the extracellular domains of these receptors may be produced starting with purified receptor or cells expressing the receptor on their surfaces.

Purified EGFR for use in producing antibodies suitable for use in the methods of the invention may be obtained from cells expressing EGFR, such as placental tissue, tumors or cell lines expressing EGFR, such as A431 carcinoma cells, Ullrich et al. Nature 309: 418–425, or the cell lines described herein. Alternatively, cells expressing EGFR on their surface may be used as the starting material for production of antibodies. Suitable cells include the cell lines disclosed herein, tumor cells expressing EGFR and other cells expressing EGFR.

Monoclonal antibodies specific for extracellular domains of EGFR may be selected by screening for binding of the antibodies to cells expressing EGFR. Antibodies binding to EGFR expressed on the surface of cells will be specific for extracellular domains of EGFR. The antibodies may be further screened by testing for binding of the antibodies to cells not expressing EGFR on their surface; no binding additionally indicating specificity for EGFR. Suitable methods for production and selection of monoclonal antibodies include the method of Richert et al. (1983) Journal of Biological Chemistry 258: 8902–8907.

p185c-neu or p185neu can be obtained from cells expressing the receptors for use in producing antibodies specific, or the cells expressing p185c-neu or p185neu may be used for producing antibodies. Suitable cells include those described herein, NIH 3T3 cells transformed by the neu gene, either the oncogenic or normal allele as described in Hung et al. (1986) Proc. Natl. Acad. Sci. USA 83: 261–264, Bargmann and Weinberg (1988) Proc. Natl. Acad. USA 85: 5394–5398, and Bargmann et al. (1986) Nature 319: 226–230.

Monoclonal antibodies specific for extracellular domains of p185c-neu or p185neu may be selected for by screening for binding of the antibodies to cells expressing p185c-neu or p185neu. Antibodies binding to p185c-neu or p185neu expressed on the surface of cells will be specific for extracellular domains of p185c-neu or p185neu. The antibodies may be further screened by testing for binding of the antibodies to cells not expressing p185c-neu or p185neu on their surface; no binding additionally indicating specificity for p185c-neu or p185neu. Suitable methods for production and selection of monoclonal antibodies include the method of Drebin et al. (1984) Nature 312: 545–548. Briefly, in this method monoclonal antibodies specific for extracellular domains of p185neu or p185c-neu may be selected for by initially screening culture supernatants from growing hybridomas for the presence of antibody capable of binding B104-1-1 cells by indirect immunofluorescence using fluorescence activated cell sorting (FACS). Positive supernatants may then be tested for specificity by determining whether they contain antibody capable of binding normal NIH 3T3 cells, or NIH 3T3 cells transformed by transfection with Harvey sarcoma virus proviral DNA (cell line XHT-1-1a).

Chimeric antibodies having a specificity for both the epidermal growth factor receptor and p185 neu, p185c-neu or a homologue of p185 neu or p185c-neu, such as erbB-2 combine specificity for two different antigens in the same molecule. Chimeric antibodies may be produced by fusing two separate monoclonal antibody producing cell lines, so that the resulting cells produce monoclonal antibodies having specificity for both antigens. Chimeric antibodies of this type may be made by procedures known in the art, such as the method in Milstein and Cuello (1984) Immunology Today 5: 299–304, the disclosures of which are specifically incorporated as if fully set forth herein.

Antibodies suitable for use in the methods of the invention may be conjugated to other types of molecules such as cytotoxic molecules to enhance the tumor-reducing properties of the antibodies or provide other means of treating the tumors. For instance, the antibodies may be conjugated with a radioactive molecule, or therapeutic molecule such as a drug or other cancer treatment.

It is within the scope of the invention to use fragments of antibodies specific for epidermal growth factor receptor, p185 neu, p185c-neu, or a homologue of p185 neu or p185c-neu that exhibit binding specificity to these receptors. It is also within the scope of the methods of the invention to use peptides bindable with epidermal growth factor receptor, p185 neu, p185c-neu, or a homologue of p185 neu or p185c-neu, such peptides comprising at least a portion of the hypervariable region of an antibody specific for epidermal growth factor receptor, p185 neu, p185c-neu, or a homologue of p185 neu or p185c-neu. These peptides may also be joined at one end by a means such as a disulfide bond to form peptide dimers having one peptide bindable with EGFR and one peptide bindable with p185 neu, p185c-neu, or a homologue of p185 neu or p185c-neu.

Experimental Procedures

Preparation of Monoclonal Antibodies Specific for p185neu $C_3H/HeJ$ mice were repeatedly immunized with NIH 3T3 transfectants transformed by the neu oncogene (cell line B104-1-1) emulsified in Freund's adjuvant. Spleens from immune mice were fused with the aminopterin-sensitive NS-1 myeloma line, and hybridomas were selected in hypoxanthine-aminopterin-thymidine media. Culture supernatants from growing hybridomas were initially screened for the presence of antibody capable of binding B104-1-1 cells by indirect immunofluorescence using fluorescence activated cell sorting (FACS). Positive supernatants were then tested for specificity by determining whether they contained antibody capable of binding normal NIH 3T3 cells, or NIH 3T3 cells transformed by transfection with Harvey sarcoma virus proviral DNA (cell line XHT-1-1a). Selection of antibodies was performed according to these methods as disclosed in Drebin et al. (1984) Nature 312: 545–548, the disclosures of which are specifically incorporated as if fully set forth herein. Five hybridomas were identified that produce monoclonal antibodies capable of specifically binding B104-1-1 cells. One of the hybridomas produces an antibody termed 7.16.4 which is an immunoglobulin of the IgG2a isotype. Antibody 7.16.4 appears to recognize a cell-surface antigenic determinant specifically expressed by cells containing the neu oncogene.

Cell Culture Techniques

Cell lines were routinely cultured in 175 mm tissue culture flasks (Corning), containing 10 ml of Dulbecco's modified Eagle's medium (DMEM<K.C. Biologicals) supplemented with 5% heat inactivated fetal calf serum, 1% pen-strep mixture (M.A. Bioproducts). Transformed cell lines were passaged twice weekly at a 1:20 dilution following release from the tissue culture dish surface with Trypsin-Versene (M.A., Bioproducts). Nontransformed NIH3T3w cells or NR6 cells were passaged in a similar fashion, but at higher dilution (1:30–1:50) to prevent the development of spontaneous transformants.

Transfection and Cell Isolation

DNA transfection into $1\times10^6$ cells was carried out by the calcium phosphate precipitation technique (Graham and Van der Eb (1973) Virology 52: 456–467. The plasmids used in this study were pSV2-neuN, prepared according to the method of Bargmann et al. (1986) Nature 319: 226–230 (contains DNA coding for p185-neu), pEGFR1 prepared according to the method of Gorman and Miyajima (1988) J. Cell Biochem. Supplement 12A, C219 (a gift from A. Miyajima, DNAX) (contains DNA coding for epidermal growth factor receptor), pSV2NEO (Southern and Berg, (1982) J. Mol. Appl. Gent. 1: 327–341, and pSV2DHFR (Hung et al. (Proc. Natl. Acad. Sci. USA 83: 261–264). Two days after transfection, the cells were split and grown in the presence of 600 μM methotrexate in Dulbecco's modified Eagle's medium containing 10% dialyzed calf serum. pEGFR1, the human EGFR cDNA is cloned under the transcriptional control of the SV40 early promotor element and the R-U5 segment of human T cell leukemia virus type 1 LTR (Takebe et al., (1988) Mol. Cell. Biol. 8: 466–472). 1 μg of pEGFR1 was used for each transfection.

Anchorage-Independent Growth Assay

Anchorage-independent growth capability was determined by assessing the colony-forming efficiency of cells suspended in soft agar according to the method in Drebin, et al. (1985) Cell 41: 695–706. All experiments to determine colony-forming efficiency were conducted using 50 mm tissue culture dishes containing a 6 ml cell free feeder layer and a 1 ml top layer in which $1\times10^3$ or $1\times10^4$ cells were suspended. Colonies were counted at 21 days for all cell lines. Each experimental group represents the mean of triplicate of quadruplicate samples.

Experimental Animals

Nude mice were obtained from Jackson Laboratories (Bar Harbor, Maine) and were housed in the Research Animal FAcility of the Department of Pathology, University of Pennsylvania School of Medicine. Animals used in this study were maintained in accordance with the guidelines of the Committee on Animals of the University of Pennsylvania and those prepared by the Committee on Care and Use of Laboratory Animals of the Institute of Laboratory Animal Resources, national Research Council (DHEW publication NIH 78-23, revised 1978).

Phosphorylation and Immunoprecipitation

All reagents were obtained from Sigma Chemical Co. (St. Louis, Mo.) unless otherwise indicated. $1\times10^6$ cells were plated, cultured for 24 hours and then incubated with inorganic $^{32}P$ (Amersham) at 0.5 mCi/ml in 5% FCS/phosphate free RPMI for 16 hours. The cells then were incubated for 15 minutes at 37° C. with each ligand at various concentrations EGF was obtained from GIBCO). Cells were washed with cold phosphate buffered saline (PBS) containing 400 uM sodium othovanadate and they lysed in PI/RIPA buffer, (1% NP40, 1% Deoxycholate, 0.1% SDS, 0.15 M NaCl, 0.01 M sodium phosphate pH 7.4, 1% Trasylol, 1 mM PMSF, 2 mM EDTA, 10 mM sodium fluoride, 10 mM sodium pyrophosphate, 400 uM sodium othrovanadate, 10 mM iodoacetoamide and 1 mM ATP0 for 30 minutes. Pre-cleared supernatants were subjected to immunoprecipitation with 7.16.4, a monoclonal antibody specific for p185neu/p185c-neu or with M294, an EGFR-specific antibody (ICN Biomedicals). Antibody 7.16.4 was prepared according to the method of Drebin et al., (1984) Nature 312: 545–548.

Immune Complex Kinase Assay $3\times10^6$ Ml cells were incubated in DMEM/5%FCS with or without 10 ng/ml EGF for 15 minutes at 37° C. Cells were washed twice with cold PBS and scraped into 1 ml of lysis buffer (1% Triton X-100, 1% Deoxycholate, 0.1% SDS, 0.15 M NaCl, 0.01M Sodium pyrophosphate pH 7.4 1% Trasylol, 1 mM PMSF, 2 mM EDTA, 10 mM sodium fluoride, 10 mM sodium pyrophosphate, 400 uM sodium orthovanadate, 10 mM iodoacetamide and 1 mM ATP) and incubated for 30 minutes. The lysates were triturated, then incubated for 10 minutes with 50 ul of 50% (v/v) Protein A-Sepharose and centrifuged for 5 minutes to preclear the lysates. Precleared supernatants were incubated with 5 μg of 7.16.4 for 30 minutes, followed by 50 ul of 50% (vol/vol) protein a-sepharose for 30 minutes with rotation. Immune complexes were collected by centrifugation and washed four times with 500 ul of washing buffer (0.1% Triton X-100, 0.4 mM EDTA 10 uM sodium fluoride, 10 mM sodium fluoride, 10 mM sodium pyrophosphate, 400 uM sodium orthovanadate, 0.01 sodium fluoride, pH 7.4) then twice with 750 ul reaction buffer (20 mM Hepes pH7.4, 3 mM $MnCl_2$, 30 uM Na3SO4, and 0.1% Triton X-100). Pellets were resuspended in 50 ul of reaction buffer and [Gamma $^{32}P$]-ATP was added to yield a final concentration of 10 uM. The samples were incubated at 27° C. for 15 minutes and the reaction terminated by addition of 3X SDS-PAGE sample buffer pH 6.8 (3% SDS, 10% Glycerol, 5% 2-mercaptoethanol, 0.4% bromphenol blue) containing 2 mM ATP and 2 mM EDTA and incubated at 100° C. for 5 minutes before SDS-PAGE analysis above.

$^{125}$I-EGF and $^{125}$I Anti-p185neu Mononclonal Antibody Binding Assays

Binding assays using lactoperoxidase iodinated EGF (43,000 cpm/ng) or highly purified antibody 7.16.4 (12,000 cpm/ng) were performed according to the method of Kokai et al. (1987) Proc. Natl Acad. Sci USA 84: 8498–8501. Data were analyzed on a Scatchard plot, and apparent $K_D$ and $B_{max}$ determined.

Scatchard analyses were performed to study the affinity states of EGF receptors on M1 and K2 cells. The binding profiles on M1 and K2 cells reveal that each clone has two different affinity states for EGF. About 8% of the receptors for EGF expressed by the clones were high affinity. The M1 and K2 $K_D$ values for EGF binding were $1.6\times10^{-11}$M and $6.0\times10^{-10}$M respectively for high affinity receptors and $3.1\times10^{-9}$M and $9.7\times10^{-8}$M respectively for the low affinity receptors (see Table 1). Table 1 shows the transformation parameters of the cell lines and summarizes the transformed phenotypes of the transfectants. For plating efficiency in soft agar, $1\times10^3$ and $1\times10^4$ cells were seeded in normal medium containing 0.25% agarose and colonies were counted after fourteen days. Results are expressed as percentage of seeded cells. Receptor numbers were determined by $^{125}$I-anti-p 185c-neu binding assays as described in Experimental Procedures. the total number o receptors per well were divided by the total number of cells per well. A 1:1 EGF to EGFR and a 1:2 anti-p185c-neu stoichiometry was assumed. The Kd's were determined by Scatchard analysis. To test for in vivo growth potential, individual clones ($10^6$ per animal) were washed, resuspended in phosphate buffered saline, and injected subcutaneously into 30 to 40 day old nude mice. Results are expressed as the number of mice developing tumors/total number of animals injected. These data show that both p185c-neu and the EGF receptors on these cells exhibit all the expected physical and functional properties including molecular weight, phosphorylation profile, tyrosine kinase activity, and ligand binding affinity.

TABLE 1

| Cell Lines | Parental Cell Lines | Morphology | Soft agar (% efficiency) | Tumor Incidence | Receptor numbers p185neu | Receptor numbers EGFR | Kd of EGFR |
|---|---|---|---|---|---|---|---|
| NR6 | — | normal | <0.1 | 0/6 | 0 | 0 | — |
| NV | NR6 | normal | <0.1 | 0/6 | $1.7 \times 10^5$ | 0 | — |
| M1 | NR6 | transformed | 0.2–1.1 | 6/6 | $1.3 \times 10^5$ | $1.4 \times 10^5$ | $1.6 \times 10^{-11}$ $3.1 \times 10^{-9}$ |

TABLE 1-continued

| Cell Lines | Parental Cell Lines | Morphology | Soft agar (% efficiency) | Tumor Incidence | Receptor numbers p185neu | EGFR | Kd of EGFR |
|---|---|---|---|---|---|---|---|
| KS | NR6 | transformed | 0.2–1.1 | 6/6 | $1.8 \times 10^5$ | $6.8 \times 10^5$ | $6.0 \times 10^{-10}$ $9.7 \times 10^{-8}$ |
| NE19 | NR6 | normal | <0.1 | 0/6 | 0 | $2.5 \times 10^5$ | nd |
| NIH3T3w | — | normal | <0.1 | 0/6 | 0 | 0 | — |
| G8 | NIH3T3w | normal | <0.1 | 0/6 | $3.4 \times 10^5$ | 0 | — |
| GEr | NIH3T3w | transformed | 1–1.2 | 6/6 | $2.0 \times 10^5$ | $4.6 \times 10^4$ | nd |
| B104-1-1 | NIH3T3w | transformed | 37.5 | 6/6 | $1.4 \times 10^{5*}$ | 0 | — |
| Rat-1 | — | normal | <0.1 | 6/6 | $1.9 \times 10^4$ | $2.8 \times 10^4$ | nd |
| A431 | — | — | nd | 0/6 | 0 | $2.6 \times 10^6$ | nd |

Tumor Growth Suppression In Effector Cell Independent Conditions

To determine whether tumor growth suppression observed in vivo was caused by antibody-mediated host cell dependent effects, the ability of the anti-receptor antibodies to suppress the transformed phenotype of the M1 and K2 cells under in vitro, effector cell independent conditions was examined. A focus-formation assay was performed, as the efficiency of growth in soft agar of M1 and K2 cells is low (<2%).

Fifty cells from each cell line were plated in 6 cm culture dishes with $1\times10^4$ of NR6 cells and cultured in the DMEM containing 2% of fetal calf serum. Sixteen hours later the medium was replaced to 2% FCS-DMEM containing growth factors and antibodies as indicated on Table 2. The media was changed every 3–4 days and morphologically transformed foci were scored on day 14. Numbers represent mean ± SD. These data were confirmed by three distinct experiments and each experiment was performed in duplicate. ++ indicates more than one hundred thousand molecules of receptors are expressed per cell. + indicates ten thousand to one hundred thousand molecules of receptors are expressed per cell.

Treatment of M1 and K2 cells with micromolar concentrations of EGF results in decreased number of foci as well as a change in cell morphology to a flatter more well spread phenotype.

Overexpression of p185c-neu in Rodent Fibroblasts Does Not Result in Transformation The transforming activity of p185c-neu in two independent rodent fibroblast cell lines, NIH3T3w and NR6 was examined. The NIH3T3w cell line is an NIH3T3 cell subclone which displays a low frequency of spontaneous tumor formation and which lacks EGF receptors. NR6 is an EGFR-negative mutant of the EGFR-positive Swiss 3T3 mouse fibroblast cell line. NR6 cells were cotransfected with pSV2-neuN, an expression vector containing the p185c-neu coding region under the control of an SV40 promotor (Bargmann et al., (1986 Nature 319: 226–230), and pSV2DHFR using the calcium-phosphate precipitation method and cells were cultured in media containing 600 μM methotrexate. After methotrexate selection, p185c-neu overexpressing cells were isolated and named NV cells. The transformed phenotype of G8 cells, which are NIH3T3w cells cotransfected with the c-neu gene and pSV2DHFR (Hung et al., (1986) Proc. Natl Acad. Sci. USA 83: 261–264) was also examined.

TABLE 2

| Cell Line | Expression Level p185c-neu | Expression Level EGFR | Control | Monoclonal Antibodies 7.16.4 1 μg/ml | 425 1 μg/ml | 9BG5 1 μg/ml | Growth Factors EGF 1 μg/ml | EGF 1 μg/ml | Insulin 1 μg/ml |
|---|---|---|---|---|---|---|---|---|---|
| M1 | ++ | ++ | 21 ± 1.4 | 11 ± 2.1 | 13 ± 1.4 | 25 ± 3.5 | 12 ± 0.7 | 21 ± 2.1 | 19 ± 2.1 |
| K2 | ++ | + | 23 ± 1.4 | 11 ± 2.1 | 10 ± 2.1 | 21 ± 2.8 | 11 ± 1.4 | 17 ± 2.8 | 20 ± 0.7 |
| GEr | ++ | ++ | 60 ± 1.4 | 27 ± 3.5 | 46 ± 2.1 | nd | 30 ± 5.6 | 58 ± 3.5 | 54 ± 5.7 |
| Ha-ras transformed NIH3T3w | none | none | 29 ± 2.1 | 27 ± 3.5 | 26 ± 2.1 | nd | 25 ± 1.4 | 28 ± 0.7 | 31 ± 4.9 |
| NV | ++ | none | 0 | 0 | 0 | nd | 0 | 0 | 0 |
| G8 | ++ | none | 0 | 0 | 0 | nd | 0 | 0 | 0 |
| NE19 | none | ++ | 0 | 0 | 0 | nd | 3 ± 0.7 | 1 ± 0 | 0 |
| NIH3T3w | none | none | 0 | 0 | 0 | nd | 0 | 0 | 0 |
| NR6 | none | none | 0 | 0 | 0 | nd | 0 | 0 | 0 |

1 μg/ml of Mab 7.16.4 or Mab425 reduced the number of foci by 50%. In addition, the M1 and K2 foci were significantly smaller than the foci in control media. Neither Mab7.16.4 nor Mab425 antibody was capable of inhibiting focus formation of a ras-transformed cell line, and the isotype matched 9BG5 monoclonal antibody could not inhibit focus-formation of either the M1 or K2 cells. These data indicate that specific effects exerted on the two receptor proteins by monoclonal antibodies result in suppression of the transformed phenotype even in the absence of effector cells.

Transfectants expressing $2\times10^5$ to $4\times10^5$ copies of p185c-neu were assayed for the transformed phenotype. Seven independent transfections were performed and 29 clones were examined for morphology, focus formation, colony formation in soft agar, and tumor formation in nude mice. Although the expression level of p185c-neu in the transfectants was comparable to those seen in certain human adenocarcinomas, none of the clones tested appeared to be transformed (see Table 1).

Overexpression of EGFR Alone In Rodent Fibroblasts Does Not Result In Cellular Transformation It has been shown that overexpression of EGFR transforms NIH3T3 cells only when EGF is added to the culture medium. Accordingly NR6 cells were transfected with an EGFR expression vector. NR6 clones which overexpressed EGFR, named NE19, were not tumorigenic and did not form foci or soft agar colonies in a medium containing 10% FCS (see Table 1). Thus, transfected EGFR alone was unable to fully transform NIH3T3w and NR6 cells. In summary, neither p185c-neu nor EGFR overexpression alone is sufficient to transform NIH3T3w or NR6 cell lines.

Transfection of EGFR Into Cells Overexpressing p185c-neu Results In Cellular Transformation To study the interaction of the two tyrosine kinases (EGFR and p185c-neu), EGFR cDNA was transfected into cloned cell lines that already express high levels of the p185c-neu. The resultant cell lines, NVEr and GEr, overexpress both p185c-neu and EGFR. These double transfectants were fully transformed by the introduction of the EGFR. However, cells which overexpress p185c-neu only (G8 and NV cells) and cells which overexpress EGFR only (NE19 cells), do not display any features of the transformed phenotype. The p185c-neu/EGFR double transfectants (GEr and two NVEr clones, M1 and K2) form foci in culture and result in tumor formation in nude mice (see Table 1).

Properties Of p185c-neu And EGFR In The Transformed Clones Overexpressing The Two Receptors p185c-neu and the EGF receptors expressed on two NVEr clones, M1 and K2 were analyzed further to characterize the receptors. A 185 kd phosphoprotein was immunoprecipitated from M1, K2, Rat-1, and IEC18 (rat epithelial) cell lines with 7.16.4, a p185neu/p185c-neu specific monoclonal antibody. Similarly, a 170 kd phosphoprotein was immunoprecipitated from M1 and K2 clones with M294, an EGFR specific antibody. These data confirm that the transfected constructs properly encode the two receptors and that these proteins are phosphorylated.

EGFR-Mediated Phosphorylation of p185c-neu

EGF induces an EGFR-mediated phosphorylation of -185c-neu on tyrosine, as well as serine and threonine. p185c-neu isolated from cells treated with EGF has enhanced tyrosine kinase activity. To determine whether this interaction occurs in the double transfectants, M1 and K2 cells were metabolically labelled and incubated with an without 50 ng/ml EGF for 15 minutes at 37° C. The p185c-neu was immunopurified from cell lysates in the presence of $Na_3VO_4$ and electrophoresed using SDS-PAGE. EGF treatment increases the phosphorylation of p185c-neu.

Tyrosine Kinase Activity of Overexpressed p185c-neu

The tyrosine kinase activity of the overexpressed p185c-neu isolated from M1 cells treated with or without EGF was examined. p185c-neu was immunopurified from cell lines treated with or without EGF in the presence of $Na_3VO_4$ and used in an immune complex kinase assay. p185c-neu from EGF-treated cells exhibits 2–3 times higher autophosphorylation activity than p185c-neu isolated from untreated cells. These data confirm that this p185c-neu/EGFR interaction occurs in the doubly transfected cells.

Effects of Monoclonal Antibodies Directed Aqainst p185 neu and EGFR On The Tumorigenic Growth Of M1 and K2 Cells Implanted Into Nude Mice M1 and K2 cells were NR6 cells transfected with cellular rat new and human EGF receptor cDNA. M1 cells express $1.3\times10^5$ molecules of p185c-neu and $1.4\times10^5$ molecules of EGF receptors, while K2 cells express $1.8\times10^5$ molecules of p185c-neu and $6.8\times10^4$ molecules of EGF receptors.

$1\times10^6$ M1 or K2 cells were implanted subcutaneously in NCR nude mice, and the mice were subcutaneously treated with monoclonal antibodies to p185neu or the EGF receptor. The monoclonal antibodies used were Mab 7.16.4 (IgG2a), which is reactive with an extracellular domain of p185neu and capable of reverting the transformed phenotype of neu oncogene transformed cells in vitro and in vivo, and Mab 425, an IgG2a antibody which binds to the extracellular domain of human EGF receptor to inhibit EGF binding and induce EGF receptor down-regulation without stimulating EGF receptor tyrosine kinase activity.

$1\times10^6$ cells were suspended in 0.1 ml of PBS or 0.1 ml of PBS containing 10 μg of monoclonal antibody and injected subcutaneously in the mid-dorsum of the mice. Each group of 6 mice received PBS or 10 μg of antibody administered subcutaneously on days 1 and 7. Growing tumors were measured with vernier calipers on every day after tumors appeared. Tumor volume was calculated as the product of tumor length, width and height. The student's T-test was used to determine the significance between groups. 30 μg of Mab 7.16.4 inhibited tumor growth of M1 and K2 cells by 80–90% ($p<0.05$). Treatment with 30 μg of MAb425 also inhibited the tumorigenic growth of M1 and K2 cells by 80–90%. Mab 7.16.4 and Mab 425 were found to have no effect on the growth of NIH3T3 cells transformed by Ha-ras. In addition, an irrelevant isotype matched monoclonal antibody, 9BG5 had no effect on the tumorigenic growth of M1 and K2 cells. In contrast to the effect of the two monoclonal antibodies, injection of high concentrations of EGF did not have any significant affect on tumor growth of either the M1 or K2 cells.

Effects of A combination of Monoclonal Antibodies Directed Against p185 neu and EGFR On The Tumorigenic Growth Of M1 and K2 Cells Implanted Into Nude Mice M1 and K2 cells were NR6 cells transfected with cellular rat neu and human EGF receptor cDNA. M1 cells express $1.3\times10^5$ molecules of p185c-neu and $1.4\times10^5$ molecules of EGF receptors, while K2 cells express $1.8\times10^5$ molecules of p185c-neu and $6.8\times10^4$ molecules of EGF receptors.

$1\times10^6$ M1 or K2 cells were implanted subcutaneously in NCR nude mice, and the mice were subcutaneously treated with monoclonal antibodies to p185neu or the EGF receptor. The monoclonal antibodies used were Mab 7.16.4 (IgG2a), which is reactive with an extracellular domain of p185neu and capable of reverting the transformed phenotype of new oncogene transformed cells in vitro and in vivo, Mab 425, an IgG2a antibody which binds to the extracellular domain of human EGF receptor to inhibit EGF binding and induce EGF receptor down-regulation without stimulating EGF receptor tyrosine kinase activity, and a combination of these two antibodies.

$1\times10^6$ cells were suspended in 0.1 ml of PBS or 0.1 ml of PBS containing 10 μg of monoclonal antibody and injected subcutaneously in the mid-dorsum of the mice. Each group of 6 mice received PBS or 10 μg of antibody administered subcutaneously on days 1 and 7. Growing tumors were measured with vernier calipers on every day after tumors appeared. Tumor volume was calculated as the product of tumor length, width and height. The student's T-test was used to determine the significance between groups.

FIG. 1 shows the effects on tumor volume of the administration of antibody 7.16.4 (-◆-), antibody 425 (-■-) and a 10 μg mixture of 7.16.4 and 425 (-◇-). The PBS control is represented as (-⊡-). Mab 7.16.4 and 425 inhibited tumor growth by 70–85 percent as compared to the control. The mixture of Mabs 7.16.4 and 425, however, inhibited tumor growth by more than 90 percent as compared to the control.

Significance

Cotransfection of cells leading to overexpression of both p185c-neu and EGFR in the same cell mediates cell transformation in a specific manner. While overexpression of p185c-neu alone or EGFR alone is not sufficient to transform NIH3T3w and NR6 cell lines, the introduction and overexpression of EGFR in cells already overexpressing p185c-neu leads to transformation. The transfectants which overexpress both p185c-neu and EGFR from foci, produce colonies in soft agar, and form tumors in nude mice. The properties of the rat p185c-neu and the EGFR expressed on the doubly transfected cell lines were examined and these receptors were found to be indistinguishable from those seen in normal cells in terms of ligand binding affinities, molecular weights, and tyrosine kinase activities. Doubly transfected cells cause tumor formation when transplanted into mice. These tumors decrease in size when monoclonal antibodies to extracellular domains of p185neu and EGFR are injected into the tumors.

The data clearly show that two previously well characterized, normal cellular proteins (p185c-neu and EGFR) act in concert to transform NIH3T3 cells when coexpressed at high levels. The data also show that tumors formed from the doubly transfected cells synergistically regress when antibodies specific for extracellular domains of the two receptors interact with the cells.

I claim:

1. A method of treating mammalian tumors wherein the cells of such tumor express both 1) epidermal growth factor receptor and 2) p185neu, p185c-neu or a homologue of p185neu or p185c-neu, said method comprising administering to a mammal having such a tumor at least one antibody specific for epidermal growth factor receptor and at least one antibody specific for p185neu, p185c-neu or a homologue of p185neu or p185c-neu or a homologue in an amount effective to reduce tumor growth, wherein said antibody specific for epidermal growth factor receptor is Mab425 and said antibody specific for p185neu, p185c-neu or a homologue of p185neu or p185c-neu is Mab 7.16.4.

2. The method of claim 1 wherein each of said antibodies is conjugated with a cytotoxic molecule.

3. The method of claim 1 wherein each of said antibodies is conjugated with a radioactive molecule.

4. A therapeutic composition for treatment of a mammalian cancer tumor having cells which express both epidermal growth factor receptor and p185neu, p185c-neu or a homologue of p185neu or p185c-neu comprising at least one antibody specific for p185neu, p185c-neu or a homologue of p185neu or p185c-neu;

at least one antibody specific for epidermal growth factor receptor; and a pharmaceutically acceptable carrier or diluent, wherein said antibody specific for epidermal growth factor receptor is Mab425 and said antibody specific for p185neu, p185c-neu or a homologue of p185neu or p185c-neu is Mab 7.16.4.

5. The composition of claim 4 wherein each of said antibodies is conjugated with a cytotoxic molecule.

6. The composition of claim 4 wherein each of said antibodies is conjugated with a radioactive molecule.

* * * * *

UNITED STATES PATENT AND TRADEMARK OFFICE

CERTIFICATE OF CORRECTION

PATENT NO. : Patent No. 5,705,157

DATED : January 6, 1998

INVENTOR(S) : Mark I. Greene

It is certified that error appears in the above-indentified patent and that said Letters Patent is hereby corrected as shown below:

Col. 9, in Table 1 Equation "$6.8 \times 10^5$" should be --$6.8 \times 10^4$ --

Signed and Sealed this

Sixteenth Day of June, 1998

Attest:

BRUCE LEHMAN

Attesting Officer

*Commissioner of Patents and Trademarks*